United States Patent [19]

Bigg et al.

[11] Patent Number: 5,364,864
[45] Date of Patent: Nov. 15, 1994

[54] 1,4-DISUBSTITUTED PIPERIDINES, THEIR PREPARATION AND THEIR APPLICATION IN THERAPY

[75] Inventors: Denis Bigg; Jean-Louis Vidaluc; Francis Calmel, all of Castres, France

[73] Assignee: Pierre Fabre Medicament, Boulogne, France

[21] Appl. No.: 888,969

[22] Filed: May 26, 1992

[30] Foreign Application Priority Data

May 27, 1991 [FR] France ............... 91 06327

[51] Int. Cl.$^5$ ............... C07D 211/26; C07D 213/16; A61K 31/445
[52] U.S. Cl. ............... 514/318; 514/331; 546/193; 546/230; 546/231
[58] Field of Search ............... 546/230, 231, 193; 514/318, 331

[56] References Cited

U.S. PATENT DOCUMENTS

| | | | |
|---|---|---|---|
| 4,057,636 | 11/1977 | Petersen | 424/263 |
| 4,370,328 | 1/1983 | Campbell et al. | 424/250 |
| 5,006,523 | 4/1991 | Atwal | 544/59 |

FOREIGN PATENT DOCUMENTS 199400 10/1986 Belgium ............... 546/231

*Primary Examiner*—Marianne M. Cintins
*Assistant Examiner*—Phyllis G. Spivack
*Attorney, Agent, or Firm*—Ladas & Parry

[57] ABSTRACT

1,4-disubstituted piperidines of formula 1:

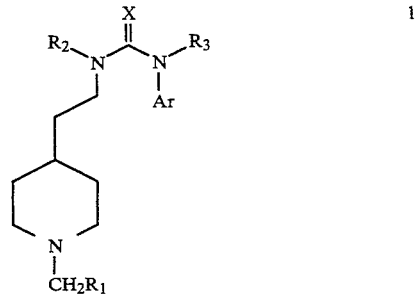

as well as the therapeutically acceptable salts of these molecules. The invention also relates to the application in therapy of the compounds of the general formula 1.

10 Claims, No Drawings

1,4-DISUBSTITUTED PIPERIDINES, THEIR PREPARATION AND THEIR APPLICATION IN THERAPY

The subject of the present invention, carried out at the Centre de Recherche Pierre Fabre, is new 1,4-disubstituted piperidines, their preparation and their application in therapy.

The compounds of the invention correspond to the general formula 1:

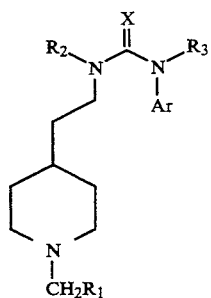

in which:

$R_1$ represents a $C_5$–$C_7$ cycloalkyl group, a phenyl group or a phenyl radical substituted by a $C_1$–$C_4$ alkyl group, a $C_1$–$C_4$ alkoxy group, a nitro radical or a halogen atom;

$R_2$ and $R_3$ represent, independently of each other, a hydrogen atom or a $C_1$–$C_4$ alkyl group;

X represents a sulfur atom, an oxygen atom, a radical CH—$NO_2$ or a radical of the general formula N—$R_4$, where $R_4$ represents a hydrogen atom, a hydroxyl group, a $C_1$–$C_4$ alkoxy group, a $C_1$–$C_4$ alkyl group, a cyano group or a $C_1$–$C_4$ alkylsulfonyl group;

Ar represents a pyridyl group or a phenyl group, optionally substituted by one or more substituents chosen from a halogen atom, a $C_1$–$C_4$ alkyl group, a $C_1$–$C_4$ alkoxy group, a $C_1$–$C_4$ acyl group, a cyano group, a nitro group, a trifluoromethyl group or a trifluoromethoxy group.

The invention also covers the salts of the compounds of the general formula 1 with pharmaceutically acceptable inorganic or organic acids. By way of non-limiting example, the acid employed may be hydrochloric acid or fumaric acid.

The compounds of general formula 1 of the invention can be prepared according to the methods described below.

The compounds of general formula 1 where X represents an oxygen atom or a sulfur atom and $R_3$ represents a hydrogen atom can be prepared by the reaction of an amine of general formula 2 with an isocyanate or isothiocyanate of general formula 3 according to the following scheme:

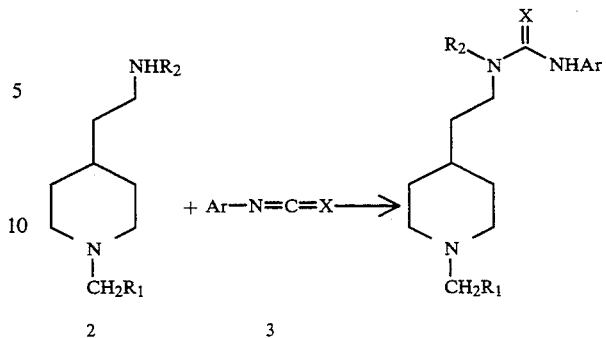

where $R_1$, $R_2$ and Ar are defined as above and X represents an oxygen or sulfur atom.

The starting amines 2 and the compounds of general formula 3 can be prepared according to known methods. The reaction of a compound of general formula 2 with an isocyanate of general formula 3 (X=O) can be carried out at a temperature of between 0° C. and 35° C. in an aprotic solvent such as dichloromethane, dichloroethane, chloroform, toluene or an ether such as tetrahydrofuran.

The reaction of a compound of general formula 2 with an isothiocyanate of formula 3 (X=S) is carried out in a solvent such as a chlorinated solvent, for example dichloromethane or dichloroethane, a ketonic solvent, an ester, an ether or an alcohol. The reaction can be carried out at room temperature or speeded up merely by warming.

The compounds of general formula 1 where X represents an oxygen atom or a sulfur atom and $R_2$ represents a hydrogen atom can be prepared by the reaction of an isocyanate or isothiocyanate of general formula 4 with an amine of general formula 5 according to the following scheme:

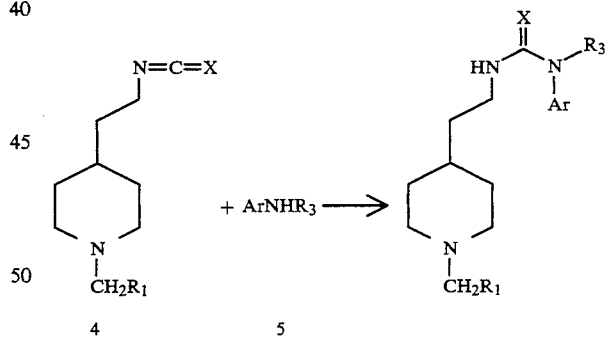

where $R_1$, $R_3$ and Ar are defined as above and X represents an oxygen or sulfur atom.

The heterocumulenes of general formula 4 and the amines of general formula 5 can be prepared according to known methods. The reaction of an isocyanate of general formula 4 (X=O) with an amine of general formula 5 can be carried out at a temperature of between 0° C. and 35° C. in an aprotic solvent such as dichloromethane, dichloroethane, chloroform, toluene or an ether such as tetrahydrofuran.

The reaction of an isothiocyanate of general formula 4 (X=S) with an amine of general formula 5 is carried out in a solvent such as a chlorinated solvent, for example dichloromethane or dichloroethane, a ketonic solvent, an ester, an ether or an alcohol. The reaction can be carried out at room temperature or speeded up merely by warming.

The compounds of general formula 1 where X represents a radical $NR_5$ ($R_5$ being a hydrogen atom, a hydroxyl group, a $C_1$-$C_4$ alkoxy group, a $C_1$-$C_4$ alkyl group or a $C_1$-$C_4$ alkylsulfonyl group) can be prepared by the reaction of a thiourea of general formula 6 with a compound of general formula 7 in the presence of mercuric oxide or of lead(II) oxide according to the following scheme:

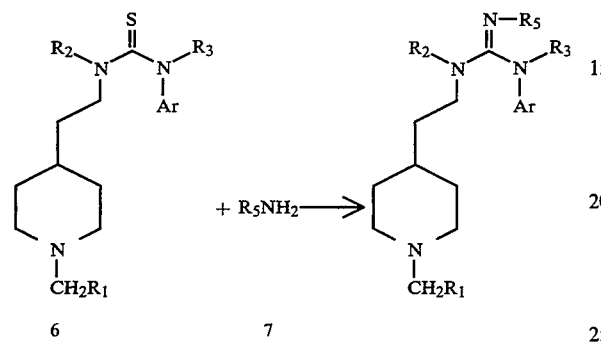

where $R_1$, $R_2$, $R_3$, $R_5$ and Ar are defined as above.

The starting thiourea 6 is treated with mercuric oxide in a chlorinated solvent such as dichloromethane or dichloroethane, and the compound of general formula 7 is then added, the reaction being carried out at room temperature.

The compounds of general formula 1 where X represents the radical N—CN can be prepared according to the following scheme:

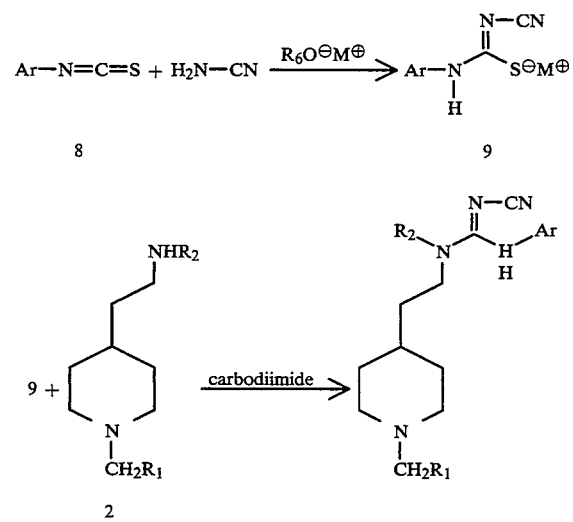

where $R_1$, $R_2$ and Ar are defined as above.

$R_6$ represents a $C_1$-$C_4$ alkyl group.

$M^\oplus$ represents $Na^\oplus$ or $K^\oplus$.

The group $R_6$ is, preferably, a methyl or ethyl group and the reaction between cyanamide and the isothiocyanate of general formula 8 is carried out while warm in methanol or ethanol. The reaction between the compound of general formula 9 thus obtained and the amine of general formula 2 is carried out in the presence of a carbodiimide at room temperature.

The compounds of general formula 1 where X represents a radical $CH$—$NO_2$ can be prepared according to the following scheme:

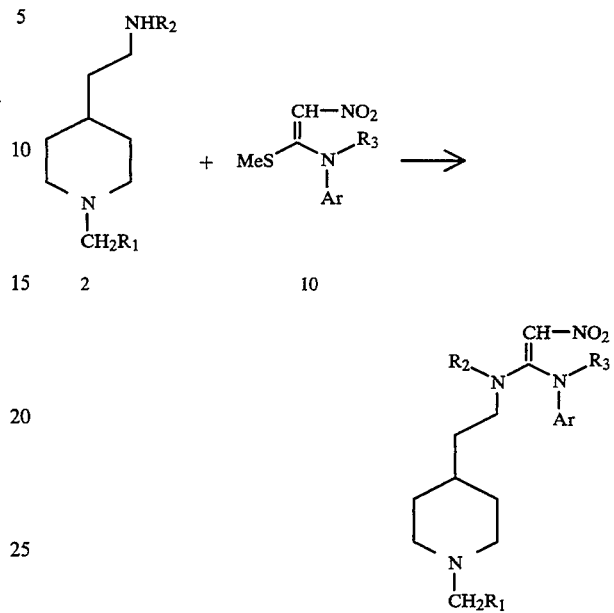

The compounds of general formula 10 can be obtained by known methods. Their reaction with an amine of general formula 2 is carried out in an organic solvent such as an alcohol, for example ethanol, preferably while warm.

The examples which follow illustrate the invention without, however, limiting the scope thereof.

EXAMPLE 1

1-Phenyl-3-[2-(1-benzyl-4-piperidyl)ethyl]thiourea: Compound No. 1; $R_1$=Ph, $R_2$=$R_3$=H, X=S, Ar=Ph.

3.0 ml (25 mmoles) of phenyl isothiocyanate are added to a solution of 5.0 g (22.9 mmoles) of 2-(1-benzyl-4-piperidyl)ethylamine in 50 ml of dichloromethane with stirring at room temperature. After an hour, the solvent is evaporated off and the amber, oily residue is taken up in ethyl ether. 7.3 g (90%) of compound 1 are obtained in the form of white crystals.

MP: 113°–115° C.

EXAMPLE 2

1-Phenyl-2-hydroxy-3-[2-(1-benzyl-4-piperidyl)ethyl]guanidine: Compound No. 2; $R_1$=Ph, $R_2$=$R_3$=H, X=NOH, Ar=Ph.

7.2 g (33.4 mmoles) of mercuric oxide are added to a solution of 5.9 g (16.7 mmoles) of 1-phenyl-3-[(1-benzyl-4-piperidyl)-2-ethyl]thiourea in 50 ml of dichloromethane. The initial orange suspension is stirred at room temperature for 30 minutes. The black s obtained is filtered and the filtrate treated with a solution of hydroxylamine (20.9 mmoles) in 20 ml of methanol. The solution is stirred at room temperature for 30 minutes. The solvent is evaporated off and the gummy green residue is taken up with dilute hydrochloric acid. The neutral impurities are extracted with dichloromethane, the solution is basified and is extracted with dichloromethane.

The extracts are dried with $Na_2SO_4$ and then evaporated to give an oil which is purified by chromatography on silica gel using a dichloromethane/ethanol- /aqueous ammonia (90/9/1) mixture as the eluent. An oil is obtained which, taken up in isopropyl ether, gives 1.4 g (24%) of compound 2 in the form of creamy-white crystals.

MP: 144°–147 ° C.

EXAMPLE 3

1-Phenyl-2-cyano-3-[2-(1-benzyl-4-piperidyl)ethyl]-guanidine: Compound No. 3; $R_1=Ph$, $R_2=R_3=H$, $X=N-CN$, $Ar=Ph$.

311 mg (7.4 mmoles) of cyanamide are added to a solution of 503 mg (7.4 mmoles) of sodium ethoxide in 10 ml of absolute ethanol. The mixture is left stirring for 1 hour and then 0.9 ml (7.4 mmoles) of phenyl isothiocyanate are added and the mixture is heated at reflux for 2 hours. It is allowed to cool and to the solution are added 2 g (9.16 mmoles) of 2-(1-benzyl-4-piperidyl)ethylamine and 1.76 g (9.18 mmoles) of N-ethyl-N'-(3-dimethylamino)propylcarbodiimide hydrochloride dissolved in 20 ml of dimethylformamide. The mixture is stirred for 1 hour at room temperature and is evaporated to dryness. The oily residue is purified by chromatography on silica gel using a dichloromethane/ethanol (90/10) mixture as eluent. 1.3 g (50%) of compound 3 are obtained in the form of white crystals.

MP: 161°–163° C.

EXAMPLE 4

N-Phenyl-N'-[2-(1-benzyl-4-piperidyl)ethyl]-1,1-diamino-2-nitroethylene: Compound No. 4; $R_1=Ph$, $R_2=R_3=H$, $X=CHNO_2$, $Ar=Ph$.

1.5 g (7.13 mmoles) of 1-phenylamino-1-methylthio-2-nitroethylene are added to a solution of 3.1 g (14.2 mmoles) of 2-(1-benzyl-4-piperidyl)ethylamine in 30 ml of methanol with stirring at room temperature. The medium is brought to reflux and, after an hour, the solvent is evaporated off. The residue is treated with an ethanolic solution of hydrochloric acid and 2.0 g of the hydrochloride of compound 4 are obtained in the form of white crystals.

MP: 220°–222° C.

EXAMPLE 5

1-(3-Nitrophenyl)-3-[2-(1-benzyl-4-piperidyl)ethyl]urea: Compound No. 5; $R_1=Ph$, $R_2=R_3=H$, $X=O$, $Ar=3-NO_2C_6H_4$.

To a solution of 10 g (4.58 mmoles) of 2-(1-benzyl-4-piperidyl)ethylamine in 10 ml of dichloromethane cooled in an ice bath is added a solution of 0.8 g (4.87 mmoles) of 3-nitrophenyl isocyanate in 10 ml of dichloromethane. The reaction mixture is left to return to room temperature and the solvent is evaporated off after 18 hours. The residue is purified by chromatography on silica gel using a dichloromethane/methanol (90/10) mixture as the eluent.

1.6 g (91%) of compound 5 are obtained in the form of a light yellow oil which, treated with ethyl ether (50 ml), gives 1.2 g (69%) of compound 4 in the form of pale yellow crystals.

MP: 152°–154° C.

Table 1 below summarizes the principal synthesized products which illustrate the invention without, however, limiting the scope thereof.

TABLE 1

| Comp. No. | $R_1$ | $R_2$ | $R_3$ | X | Ar | Salt | MP (°C.) |
|---|---|---|---|---|---|---|---|
| 1 | $C_6H_5$ | H | H | S | $C_6H_5$ | base | 113–5 |
| 1 | $C_6H_5$ | H | H | S | $C_6H_5$ | HCl | 174–5 |
| 2 | $C_6H_5$ | H | H | NOH | $C_6H_5$ | base | 144–7 |
| 3 | $C_6H_5$ | H | H | N—CN | $C_6H_5$ | base | 161–3 |
| 4 | $C_6H_5$ | H | H | $CH.NO_2$ | $C_6H_5$ | HCl | 220–2 |
| 5 | $C_6H_5$ | H | H | O | $3-NO_2.C_6H_4$ | base | 152–4 |
| 6 | $C_6H_5$ | H | Me | O | $C_6H_5$ | base | Oil |
| 7 | $C_6H_5$ | H | Me | S | $C_6H_5$ | base | 62–3 |
| 8 | $C_6H_5$ | Me | H | S | $C_6H_5$ | fumarate | 147–8 |
| 9 | $C_6H_5$ | H | H | S | $4-MeO.C_6H_4$ | fumarate | 163–4 |
| 10 | $C_6H_5$ | H | H | S | $3-NO_2.C_6H_4$ | fumarate | 158–60 |
| 11 | $C_6H_5$ | H | H | S | $4-MeCO.C_6H_4$ | HCl | 190–5 |
| 12 | $C_6H_5$ | H | H | S | $2-Me.C_6H_4$ | base | 99–100 |
| 13 | $C_6H_5$ | H | H | S | $2F.C_6H_4$ | base | 111–2 |
| 14 | $C_6H_5$ | H | H | S | $3-CF_3.C_6H_4$ | fumarate | 160–5 |
| 15 | $C_6H_5$ | H | H | S | $C_6F_5$ | HCl | 235–40 |
| 16 | cyclohexyl | H | H | S | $3,4-(MeO)_2.C_6H_3$ | base | 169–70 |
| 17 | cyclohexyl | H | H | S | $4-CF_3O.C_6H_4$ | base | 125–6 |
| 18 | cyclohexyl | H | H | S | $C_6H_5$ | base | 116–7 |
| 19 | $3-NO_2.C_6H_4$ | H | H | S | $3,4-(MeO)_2.C_6H_3$ | base | 128–30 |
| 20 | $3-NO_2.C_6H_4$ | H | H | S | $3-CN.C_6H_4$ | fumarate | 155–70 |
| 21 | $C_6H_5$ | H | H | NOMe | $C_6H_5$ | base | Oil |
| 22 | $C_6H_5$ | H | H | NH | $C_6H_5$ | base | 137–8 |
| 23 | $C_6H_5$ | H | H | NPr | $C_6H_5$ | fumarate | 113–6 |
| 24 | $C_6H_5$ | H | H | $NSO_2Me$ | $C_6H_5$ | base | Oil |
| 25 | $C_6H_5$ | H | H | S | 2-pyridyl | base | 128–30 |
| 26 | $C_6H_5$ | H | H | S | 3-pyridyl | base | 136–7 |
| 27 | $C_6H_5$ | H | H | S | 4-pyridyl | base | 174–5 |

The compounds of the invention were subjected to pharmacological tests which showed their significance as acetylcholinesterase inhibitors. For this purpose, the compounds were studied according to the method described by G. L. Ellman et al., Biochem. Pharmacol., 7, 88–95 (1961).

The results obtained with some compounds of the invention are reported, by way of example, in Table 2.

TABLE 2

| Inhibition of acetylcholinesterase activity | |
|---|---|
| Compound No. | $IC_{50}$ (μM) |
| 1 | 0.32 |
| 4 | 0.08 |
| 9 | 0.15 |
| 25 | 0.02 |
| Tacrine | 0.12 |

The compounds of the invention are acetylcholinesterase inhibitors; also, they can be useful in the treatment of illnesses such as myasthenia, memory disorders and dementias, such as senile dementias or Alzheimer's disease.

The pharmaceutical preparations containing these active substances can be formulated for administration orally, rectally, parenterally or locally, for example in the form of capsules, tablets, granules, hard gelatin capsules, liquid solutions, syrups or drinkable suspensions, and may contain the appropriate excipients.

It is also possible to include therein other pharmaceutically and therapeutically acceptable active substances.

We claim:

1. A 1,4-disubstituted piperidine corresponding to the general formula 1:

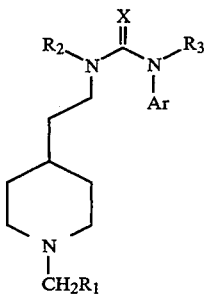

in which:
- $R_1$ represents a $C_5$–$C_7$ cycloalkyl or phenyl group, said phenyl optionally substituted by a $C_1$–$C_4$ alkyl group, a $C_1$–$C_4$ alkoxy group, a nitro group or a halogen atom;
- $R_2$ and $R_3$ represent, independently of each other, a hydrogen atom or a $C_1$–$C_4$ alkyl group;
- X represents a sulfur atom, an oxygen atom, a CH—$NO_2$ group or a group of the general formula N—$R_4$, where $R_4$ represents a hydrogen atom, a hydroxyl group, a $C_1$–$C_4$ alkoxy group, a $C_1$–$C_4$ alkyl group, a cyano group or a $C_1$–$C_4$ alkylsulfonyl group;
- Ar represents a pyridyl group or a phenyl group, said phenyl group optionally substituted by one or more substituents chosen from a halogen atom, a $C_1$–$C_4$ alkyl group, a $C_1$–$C_4$ alkoxy group, a $C_1$–$C_4$ acyl group, a cyano group, a nitro group, a trifluoromethyl group or a trifluoromethoxy group;

as well as therapeutically acceptable organic or inorganic salts of these compounds.

2. The compound of general formula 1 as claimed in claim 1, wherein the compound is a member of the group consisting of:
- 1-Phenyl-3-[2-(1-benzyl-4-piperidyl)ethyl]thiourea
- 1-Phenyl-2-hydroxy-3-[2-(1-benzyl-4-piperidyl)ethyl]guanidine
- N-1-Phenyl-N'-[2-(1-benzyl-4-piperidyl)ethyl]-1,1-diamino-2-nitroethylene
- 1-(3-Nitrophenyl)-3-[2-(1-benzyl-4piperidyl)ethyl]urea
- 1-Methyl-1-phenyl-3-[2-(1-benzyl-4-piperidyl)ethyl]urea
- 1-Methyl-1-phenyl-3-[2-(1-benzyl-4-piperidyl)ethyl]thiourea
- 1-Phenyl-3-[2-(1-benzyl-4-piperidyl)ethyl]-3-methylthiourea
- 1-(4-Methoxyphenyl)-3-[2-(1-benzyl-4-piperidyl)ethyl]-thiourea
- 1-(3-Nitrophenyl)-3-[2-(1-benzyl-4-piperidyl)ethyl]thiourea
- 1-(4-Acetylphenyl)-3-[2-(1-benzyl-4-piperidyl)ethyl]thiourea
- 1-(2-Methylphenyl)-3-[2-(1-benzyl-4-piperidyl)ethyl]thiourea
- 1-(2-Fluorophenyl)-3-[2-(1-benzyl-4-piperidyl)ethyl]thiourea
- 1-(3-Trifluoromethylphenyl)-3-[2-(1-benzyl-4-piperidyl))ethyl]thiourea
- 1-Pentafluorophenyl-3-[2-(1-benzyl-4-piperidyl)ethyl]thiourea
- 1-(3,4-Dimethoxyphenyl)-3-[2-(1-cyclohexylmethyl-4-piperidyl)ethyl]thiourea
- 1-(4-Trifluoromethoxyphenyl)-3-[2-(1-cyclohexylmethyl-4-piperidyl)ethyl]thiourea
- 1-Phenyl-3-[2-(1-cyclohexylmethyl-4-piperidyl)ethyl]thiourea
- 1-(3,4-Dimethoxyphenyl)-3-[2-{1-(3-nitrophenylmethyl)-4-piperidyl}ethyl]thiourea
- 1-(3-Cyanophenyl)-3-[2-{1-(3-nitrophenylmethyl)-4-piperidyl}ethyl]thiourea
- 1-Phenyl-2-methoxy-3-[2-(1-benzyl-4-piperidyl)ethyl]guanidine
- 1-Phenyl-3-[2-(1-benzyl-4-piperidyl)ethyl]guanidine
- 1-Phenyl-2-propyl-3-[2-(1-benzyl-4-piperidyl)ethyl]guanidine
- 1-Phenyl-2-methylsulfonyl-3-[2-(1-benzyl-4-piperidyl)ethyl]guanidine
- 1-(2-Pyridyl)-3-[2-(1-benzyl-4-piperidyl)ethyl]thiourea
- 1-(3-Pyridyl)-3-[2-(1-benzyl-4-piperidyl)ethyl]thiourea and
- 1-(4-Pyridyl)-3-[2-(1-benzyl-4-piperidyl)ethyl]thiourea.

3. A pharmaceutical composition, which contains the compound of claim 1.

4. The pharmaceutical composition, which contains the compound of claim 1 in combination with a pharmaceutically acceptable excipient.

5. 1,4-disubstituted piperidine as claimed in claim 1, wherein X represents a sulfur atom, an oxygen atom, a CH—$NO_2$ radical or a radical of the general formula N—$R_4$, where $R_4$ represents a hydrogen atom, a hydroxyl group, a $C_1$–$C_4$ alkoxy group, a $C_1$–$C_4$ alkyl group, or a $C_1$–$C_4$ alkylsulfonyl group.

6. 1,4-disubstituted piperidine as claimed in claim 1, wherein X represents a sulfur atom.

7. 1,4-disubstituted piperidine as claimed in claim 5, wherein $R_1$ represents a phenyl radical.

8. 1,4-disubstituted piperidine as claimed in claim 1, wherein X represents a CH—$NO_2$ radical.

9. 1,4-disubstituted piperidine as claimed in claim 8, wherein $R_1$ represents a phenyl radical.

10. A method for inhibiting acetylcholinesterase activity in a host which comprises administering an effective amount of a compound according to claim 1 to said host.

* * * * *